United States Patent

Konomura et al.

(10) Patent No.: US 9,429,526 B2
(45) Date of Patent: *Aug. 30, 2016

(54) BLADE INSPECTION APPARATUS

(71) Applicant: OLYMPUS CORPORATION, Shibuya-ku, Tokyo (JP)

(72) Inventors: Yutaka Konomura, Tachikawa (JP); Eiichi Kobayashi, Tama (JP); Fumio Hori, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,760

(22) Filed: Jul. 21, 2014

(65) Prior Publication Data

US 2015/0036127 A1 Feb. 5, 2015

(30) Foreign Application Priority Data

Aug. 1, 2013 (JP) .................................. 2013-160752

(51) Int. Cl.
  *G01N 21/00* (2006.01)
  *G01N 21/95* (2006.01)
  *G02B 23/24* (2006.01)
  (Continued)

(52) U.S. Cl.
  CPC .............. *G01N 21/95* (2013.01); *F01D 5/005* (2013.01); *G01N 21/954* (2013.01); *G02B 23/2476* (2013.01); *F05D 2230/72* (2013.01); *F05D 2270/8041* (2013.01)

(58) Field of Classification Search
  CPC ...... G82B 23/24; F81D 5/88; G81N 21/954; H04N 13/00; A61B 1/008; G06F 15/00; G01J 5/00

USPC .......... 356/241.6, 614–615, 241.1; 600/138, 600/114
See application file for complete search history.

(56) References Cited

U.S. PATENT DOCUMENTS 4,659,195 A    4/1987 D'Amelio et al.
4,784,463 A    11/1988 Miyazaki
(Continued)

FOREIGN PATENT DOCUMENTS

DE    3707468 A1    9/1987
DE    19513930 A1    9/1996
(Continued)

OTHER PUBLICATIONS

Extended European Search Report dated Dec. 12, 2014 issued in counterpart European Application No. 14178329.0.
(Continued)

*Primary Examiner* — Tarifur Chowdhury
*Assistant Examiner* — Isiaka Akanbi
(74) *Attorney, Agent, or Firm* — Holtz, Holtz & Volek PC

(57) ABSTRACT

A blade inspection apparatus inspects a plurality of blades periodically disposed on a periphery of a rotating shaft of a rotor of an engine and rotated on the rotating shaft. The blade inspection apparatus has a borescope having an insertion portion in which an observation optical system is provided, fixtures attached to one of a plurality of external access ports provided on the engine and fixing the borescope, and dedicated for each of the external access ports, and an identification information output portion for outputting identification information for identifying the external access port to which the fixtures are attached.

15 Claims, 8 Drawing Sheets

(51) Int. Cl.
*G01N 21/954* (2006.01)
*F01D 5/00* (2006.01)

(56) References Cited

U.S. PATENT DOCUMENTS

| | | | |
|---|---|---|---|
| 5,028,117 A | 7/1991 | Muhlenkamp-Becker | |
| 5,096,292 A | 3/1992 | Sakamoto et al. | |
| 5,102,221 A | 4/1992 | Desgranges et al. | |
| 5,155,941 A | 10/1992 | Takahashi et al. | |
| 5,335,061 A | 8/1994 | Yamamoto et al. | |
| 5,575,754 A | 11/1996 | Konomura | |
| 7,231,817 B2 | 6/2007 | Smed et al. | |
| 7,518,632 B2 | 4/2009 | Konomura | |
| 8,314,834 B2 | 11/2012 | Konomura | |
| 8,714,038 B2 | 5/2014 | Moran et al. | |
| 2001/0012053 A1* | 8/2001 | Nakamura | 348/45 |
| 2002/0161284 A1 | 10/2002 | Tanaka | |
| 2004/0176661 A1 | 9/2004 | Futatsugi | |
| 2005/0014996 A1 | 1/2005 | Konomura et al. | |
| 2006/0149126 A1 | 7/2006 | Ertas et al. | |
| 2006/0173243 A1* | 8/2006 | Watanabe | 600/141 |
| 2007/0171406 A1 | 7/2007 | Stokes | |
| 2008/0262311 A1 | 10/2008 | Itou et al. | |
| 2010/0087708 A1 | 4/2010 | Chen et al. | |
| 2012/0098940 A1 | 4/2012 | Zombo et al. | |
| 2012/0101769 A1* | 4/2012 | Zombo et al. | 702/135 |
| 2012/0184814 A1 | 7/2012 | Ebata et al. | |
| 2013/0008233 A1 | 1/2013 | Kosugi et al. | |
| 2013/0135457 A1 | 5/2013 | Kell et al. | |
| 2015/0002841 A1 | 1/2015 | Kobayashi et al. | |
| 2015/0035968 A1 | 2/2015 | Kobayashi et al. | |

FOREIGN PATENT DOCUMENTS

| | | |
|---|---|---|
| EP | 1811136 A2 | 7/2007 |
| EP | 2485079 A1 | 8/2012 |
| EP | 2597273 A2 | 5/2013 |
| GB | 2033973 A | 5/1980 |
| JP | 04267213 | 9/1992 |
| JP | 2007163723 A | 6/2007 |
| JP | 2011039193 A | 2/2011 |
| WO | 2013045108 A1 | 4/2013 |

OTHER PUBLICATIONS

Related U.S. Appl. No. 13/929,564; First Named Inventor: Yutaka Konomura; Title: "Endoscope System"; filed Jun. 27, 2013.
Related U.S. Appl. No. 14/336,680; First Named Inventor: Yutaka Konomura; Title: "Blade Inspection System"; filed Jul. 21, 2014.

* cited by examiner

BLADE INSPECTION APPARATUS

CROSS REFERENCE TO RELATED APPLICATION

This application claims benefit of Japanese Application No. 2013-160752 filed in Japan on Aug. 1, 2013, the entire contents of which are incorporated herein by this reference.

BACKGROUND OF THE INVENTION

1. Field of the Invention

The present invention relates to a blade inspection apparatus and particularly relates to a blade inspection apparatus for inspecting a blade of an engine.

2. Description of the Related Art

Recently, in inspecting a blade of a jet engine and the like, such a practice that an endoscope is inserted into the jet engine, an inspection image of the blade is obtained, and the blade is inspected is widely performed.

In the blade inspection, an inspector inserts an insertion portion of the endoscope into a plurality of external access ports provided in a casing of the engine, and the inspector advances a distal end portion of the insertion portion to an observation target portion, while he/she watches the inspection image of an inside of the engine displayed on a monitor. That is, the inspector inserts the insertion portion into each of the external access ports, and the inspector inspects presence of a scratch and the like at a predetermined portion of the blade in the engine or over a predetermined inspection range from the predetermined portion, while he/she watches the inspection image displayed on the monitor.

Moreover, as disclosed in Japanese Patent Application Laid-Open Publication No. 2007-163723, a technology in which a fixing tool is attached to the external access port, and the insertion portion of the endoscope is inserted into the engine is proposed. The fixing tool is installed with two pressing plates brought into contact with a wall surface of the jet engine, and the insertion portion of the endoscope apparatus is inserted and fixed to the external access port.

SUMMARY OF THE INVENTION

A blade inspection apparatus of an aspect of the present invention is a blade inspection apparatus for inspecting a plurality of blades periodically disposed on a periphery of a rotating shaft of a rotor of an engine and rotated on the rotating shaft and has an endoscope having an insertion portion in which an observation optical system is provided, a fixture attached to one of a plurality of external access ports provided on the engine and fixing the endoscope, and dedicated for each of the external access ports, and an identification information output portion for outputting identification information for identifying the external access port to which the fixture is attached.

DETAILED DESCRIPTION OF THE PREFERRED EMBODIMENTS

Figure 1:
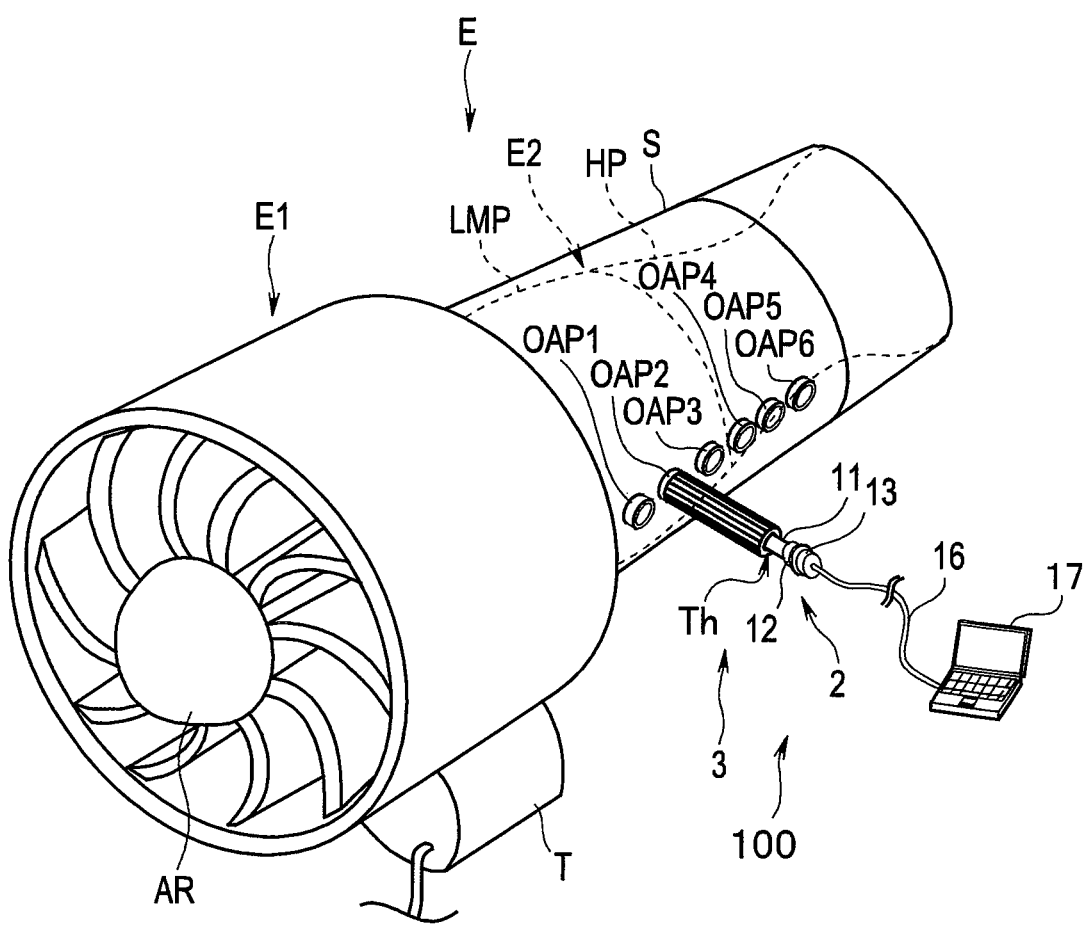
FIG. 1 is a perspective view illustrating a state of an inspection of a jet engine according to a first embodiment of the present invention.

Embodiments of the present invention will be described below by referring to the drawings.

Note that, in the following explanation, the figures based on the embodiments are schematic, and a relationship between a thickness and a width of each portion, a ratio of a thickness among the respective portions and the like are different from actual ones, and even among the figures, those with different relationships of dimensions or different ratios might be included.

First Embodiment

System Configuration

First, a blade inspection system 100 of the embodiment of the present invention will be described below on the basis of the drawings.

Figure 2:
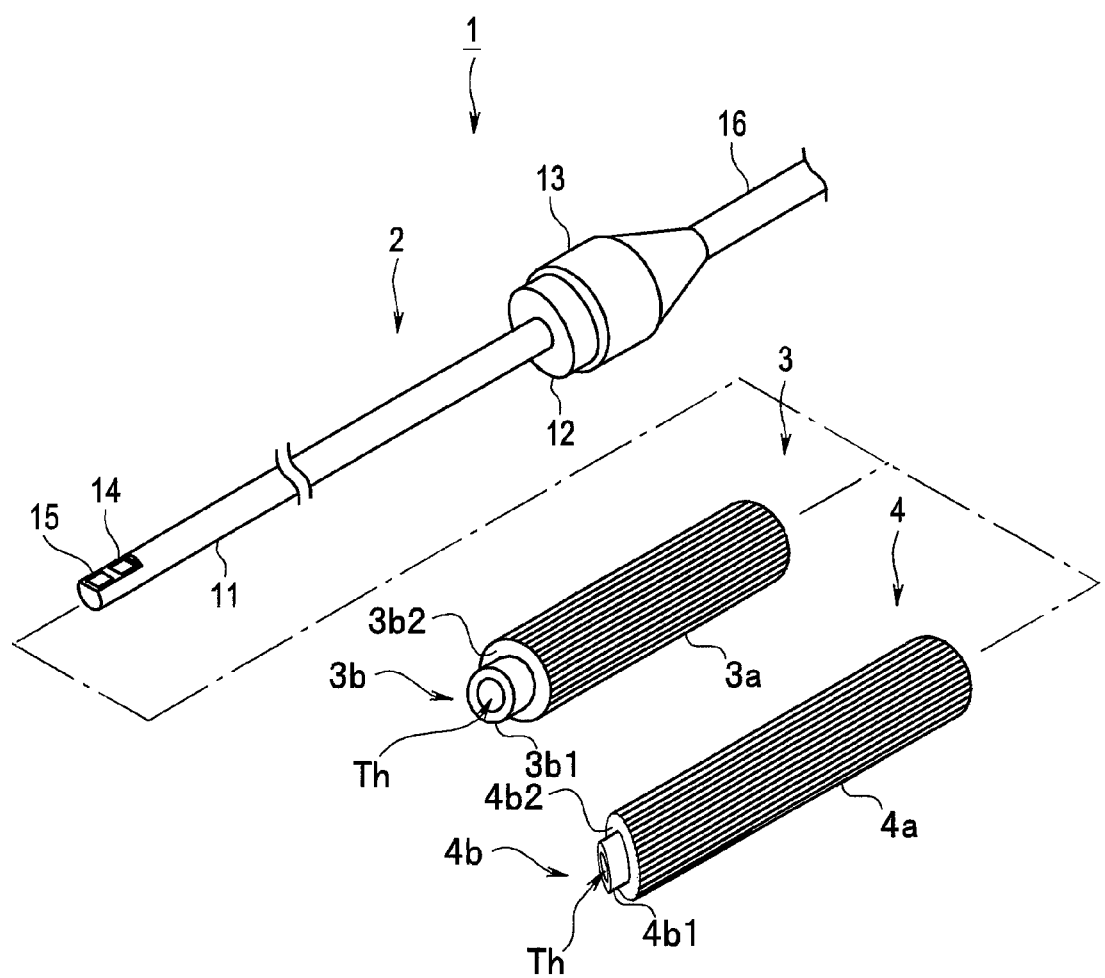
FIG. 2 is a perspective view illustrating an entire configuration of a blade inspection apparatus according to the first embodiment.

FIG. 1 is a perspective view illustrating a state of an inspection of a jet engine. FIG. 2 is a perspective view illustrating an entire configuration of a blade inspection apparatus. An engine E has, as illustrated in FIG. 1, from an intake side toward an exhaust side, an intake portion E1, a compressor portion E2, a combustion portion, and an exhaust portion (neither is shown in detail).

The compressor portion E2 is covered by a cylindrical skin S which becomes an exterior cover. The compressor portion E2 is an axial-flow type compressor and has a plurality of stages, in which a low-to-medium pressure compressor portion LMP and a high-pressure compressor portion HP are disposed in order from the intake side toward the exhaust side therein.

In the skin S, a plurality of or six, here, external access ports OAP 1 to 6 are provided. The six external access ports OAP 1 to 6 include the two external access ports OAP 2 and 3 which become mounting ports for a first fixture 3 and a second fixture 4. At hole portions of these external access ports OAP 2 and 3, the first fixture 3 and the second fixture 4 are attached, respectively, and mounted. In FIG. 1, only the first fixture 3 is illustrated.

The fixture to be attached to each of the external access ports OAP has an insertion hole Th through which an insertion portion 11 of a borescope 2 which is an endoscope can be inserted. The borescope 2 is inserted into the inside of the compressor portion E2 through the insertion hole Th of the fixture.

Therefore, an inspector can inspect a plurality of rotor blades RB or stator vanes SV (see FIG. 3) inside the compressor portion E2 of the engine E by the first fixture 3 or the second fixture 4 and the borescope 2 of the blade inspection system 100.

Moreover, the endoscopic inspection is performed by connecting a turning tool T to the engine E. The turning tool T is an apparatus for rotating a rotating shaft AR, includes a motor and a gearbox, and can rotate the rotating shaft AR through a shaft (not shown).

Then, in the endoscopic inspection, while the plurality of rotor blades are rotated around the rotating shaft AR by using the turning tool T, the plurality of rotor blades provided on the rotating shaft AR are photographed by the borescope 2 inserted into the compressor portion E2 and the endoscopic inspection is conducted.

Thus, the blade inspection system 100 is a blade inspection system for inspecting the plurality of blades periodically disposed on a periphery of the rotating shaft of the rotor of the engine E and rotated on the rotating shaft. Then, the blade inspection system 100 includes the borescope 2 which is an endoscope having the insertion portion 11 in which an observation optical system is provided, a plurality of the fixtures 3, 4 and the like to be mounted on the external access ports OAP different from each other of the engine E for guiding the insertion portion 11 of the borescope 2 into the engine E, and a personal computer (PC) 17 connected to the borescope 2.

As illustrated in FIG. 2, the blade inspection apparatus 1 mainly has the borescope 2 as the endoscope and the plurality of fixtures 3, 4 and the like to be mounted on a jet engine or the like as an inspection target.

The fixture to be attached to each of the external access ports OAP of each engine is determined in advance for each of the external access ports OAP. That is, each of the fixtures is a fixture dedicated for the corresponding external access port. A configuration of the fixture will be described later.

In FIG. 2, only two fixtures or the fixture (hereinafter referred to as a first fixture) 3 and the fixture (hereinafter referred to as a second FIG. 4, here, are illustrated. In the following explanation, too, these two fixtures will be explained as examples.

The borescope 2 is a side-view type endoscope and has a cylindrical insertion portion 11 in which an observation window 14 and an illumination window 15 are provided on a side part of a distal end portion and an eyepiece portion 12 disposed at a proximal end portion of the insertion portion 11. Note that, here, a detachable image pickup apparatus 13 is mounted to the eyepiece portion 12 of the borescope 2. Inside the borescope 2, observing means and illuminating means are disposed. More specifically, in the insertion portion 11 of the borescope 2, a mirror, an objective optical system, a relay optical system, and an LED and the like as the illuminating means are disposed as an observation optical system. Note that, in the observation window 14 and the illumination window 15, transparent members such as glass are provided.

In the eyepiece portion 12 of the borescope 2, an eyepiece optical system for visualizing an image transmitted by the relay optical system is provided. In the image pickup apparatus 13 as a camera mounted on the eyepiece portion 12, an image pickup optical system and a solid-state image pickup device 21 (FIG. 4) are disposed. The image pickup optical system forms an image of an object visualized by the eyepiece portion 12 of the borescope 2. The solid-state image pickup device 21 picks up an image of the object formed by the image pickup optical system.

An image pickup signal which is a video signal photo-electrically converted in the solid-state image pickup device 21 is outputted to a personal computer (PC) 17 via a signal cable 16. Note that the image pickup signal from the solid-state image pickup device 21 may be configured to be outputted to a video processor or the like via the signal cable 16.

Since the configurations of the borescope 2 and the image pickup apparatus 13 described above are known, detailed explanation of the other configurations will be omitted.

(Configuration of Fixture)

Subsequently, a configuration of the fixture will be explained. The two fixtures 3 and 4 will be mainly explained below.

The fixture 3 has a cylindrical body portion 3a and a fitting portion 3b to be fitted in the hole of the external access port OAP 2. The fitting portion 3b has a shape fitted only in the hole of the external access port OAP 2 among the six external access ports OAP 1 to 6 of the engine E. Thus, since the fitting portion 3b is fitted only in the hole of the external access port OAP 2, the fixture 3 cannot be attached to the other external access ports OAP 1 and 3 to 6 of the engine E.

The fitting portion 3b has a projection portion 3b1 fitted in the hole of the external access port OAP 2 and a bottom surface portion 3b2 matching the shape of an outer surface of the external access port OAP 2 and to be in close contact therewith. By fitting the projection portion 3b1 in the hole of the external access port OAP 2 and by bringing the bottom surface portion 3b2 into close contact with the outer surface of the external access port OAP 2, the fixture 3 can be firmly attached to the external access port OAP 2.

Moreover, in the body portion 3a of the fixture 3, an identification information output portion 3c (FIG. 4) is embedded. The identification information output portion 3c is an IC chip for RFID including a circuit for transmitting predetermined identification information wirelessly in a communication method conforming to a predetermined near field communication standard, for example. Here, the identification information is a port number information of the external access port OAP 2 to which the fixture 3 is attached or "P2", for example.

The fixture 4 has a cylindrical body portion 4a and a fitting portion 4b to be fitted in the hole of the external access port OAP 3. The fitting portion 4b has a shape fitted only in the hole of the external access port OAP 3 among the six external access ports OAP 1 to 6 of the engine E. Thus, since the fitting portion 4b is fitted only in the hole of the external access port OAP 3, the fixture 4 cannot be attached to the other external access ports OAP 1, 2, and 4 to 6 of the engine E.

The fitting portion 4b has a projection portion 4b1 fitted in the hole of the external access port OAP 3 and a bottom surface portion 4b2 matching the shape of an outer surface of the external access port OAP 3 and to be in close contact therewith. By fitting the projection portion 4b1 in the hole of the external access port OAP 3 and by bringing the bottom surface portion 4b2 into close contact with the outer surface of the external access port OAP 3, the fixture 4 can be firmly attached to the external access port OAP 3.

Moreover, in the body portion 4a of the fixture 4, an identification information output portion 4c (FIG. 4) is embedded. The identification information output portion 4c is a circuit for transmitting predetermined identification information wirelessly in a communication method conforming to the near field communication standard, for example. The identification information is identification information of the external access port OAP 3 to which the fixture 4 is attached or "P3", for example.

Therefore, each of the fixtures to be attached to each of the plurality of external access ports OAP 1 to 6 is a fixture dedicated for each of the external access ports OAP for fixing the borescope 2 which is an endoscope attached to any one of the plurality of external access ports OAP 1 to 6 provided on the engine E. Then, the identification information output portion provided at each of the fixtures constitutes the identification information output portion for outputting the identification information for identifying the external access port OAP to which the fixture is attached.

The fixtures 3 and 4 have lengths different from each other along axial directions of the body portions 3a and 4a. That is because an observation window of the insertion portion of the borescope 2 comes to a position for observing a predetermined portion to be observed in the blade only by attaching the common borescope 2 to each of the fixtures even if a distance from each of the external access ports to the position for observing the predetermined portion to be observed in the blade as the observation target is different from each other.

Figure 3:
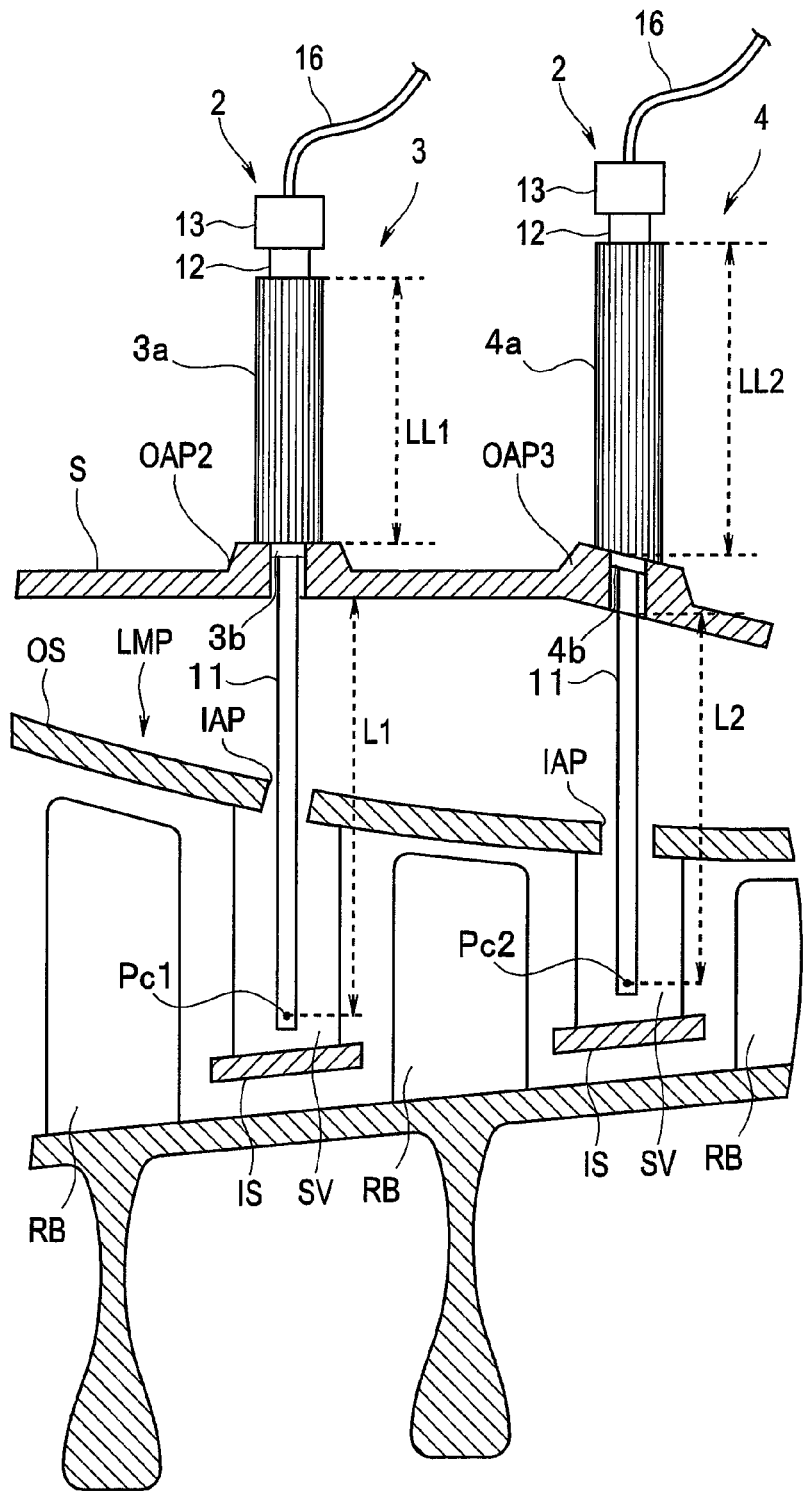
FIG. 3 is a diagram for explaining a state in which a first fixture 3 and a second fixture 4 to which a borescope 2 is mounted, respectively, according to the first embodiment, are attached to corresponding external access ports.

FIG. 3 is a diagram for explaining a state in which the first fixture 3 and the second fixture 4 on which the borescope 2 is mounted, respectively, are attached to the corresponding external access ports, respectively.

The first fixture 3 is attached to the external access port OAP 2, and the second fixture 4 is attached to the external access port OAP 3.

The portion of reference to be observed of the blade is a root portion which is a root part of the blade extending in a radial direction from the rotor, for example. Observation of the blade is performed from such portion of reference in many cases.

Thus, by using the dedicated fixture for each of the external access ports as described above, only by inserting and mounting the borescope 2 in each of the fixtures, the observation window of the insertion portion 11 of the borescope 2 is positioned to the position for observing a portion which becomes a reference of the observation, and thus, the inspector does not have to adjust the position of the observation window of the insertion portion 11 while watching an inspection image but can start inspection of the blade in a short time.

More specific explanation will be given. In the case of an engine structure illustrated in FIG. 3, by means of the borescope 2 inserted from the external access port OAP 2, a reference position Pc1 of the observation window 14 of the insertion portion 11 for observing the root portion which is a reference portion is a position away from the lower surface of the skin S by a distance L1, by means of the borescope 2 inserted from the external access port OAP 3, a reference position Pc2 of the observation window of the insertion portion 11 for observing the root portion which is a reference portion is a position away from the lower surface of the skin S by a distance L2.

Then, in order that the reference position of the observation window of the borescope 2 coincides with the reference position of the observation of each of the external access ports OAP when the common borescope 2 is inserted into different fixtures, the lengths of the body portions 3b and 4b along the axial direction are different so that a length from the outer surface of the external access port OAP to a distal end face of the eyepiece portion 12 brought into contact with the fixture is different between the fixtures 3 and 4 when the common borescope 2 is inserted into each of the fixtures 3 and 4.

In FIG. 3, when the borescope 2 is attached to each of the fixtures, a length of a portion of the fixture 3 extending to the outside of the engine E is LL1, and a length of a portion of the fixture 4 extending to the outside of the engine E is LL2. Here, as illustrated in FIG. 3, each of the lengths LL1 and LL2 is a distance from an end face of the eyepiece portion 12 to the outer surface of the external access port OAP, respectively.

That is, the length LL1 of each of the body portions 3b is set such that, when the insertion portion 11 is inserted into the insertion hole of the fixture 3, and the eyepiece portion 12 is brought into contact with the body portion 3b so that the borescope 2 is attached to the fixture 3, the reference position for observation of the distal end portion of the insertion portion 11 of the borescope 2 becomes the position Pc1 which becomes a reference for observing a predetermined portion (a root portion, for example) of the blade by the borescope 2 inserted from the external access port OAP 2.

Similarly, the length LL2 is set such that, when the insertion portion 11 is inserted into the insertion hole of the fixture 4, and the eyepiece portion 12 is brought into contact with the body portion 4b so that the borescope 2 is attached to the fixture 4, the reference position for observation of the distal end portion of the insertion portion 11 of the borescope 2 becomes the position Pc2 which becomes a reference for observing a predetermined portion (a root portion, for example) of the blade by the borescope 2 inserted from the external access port OAP 3.

Therefore, the inspector does not have to perform the prior-art cumbersome operation of inserting the insertion portion 11 to the position for picking up an image of the portion which becomes the reference for observation of the blade while watching an inspection image displayed on a monitor but can perform that in a short time.

The two fixtures 3 and 4 are explained as above but the same applies to the other fixtures. That is, each of the fixtures is a dedicated device corresponding to the external access port determined in advance, and the reference position for observation of the borescope 2 in the engine coincides with the position for observing the portion which becomes the reference for observation of the blade for each of the external access ports OAP to whichever fixture the common borescope is inserted.

Figure 4:
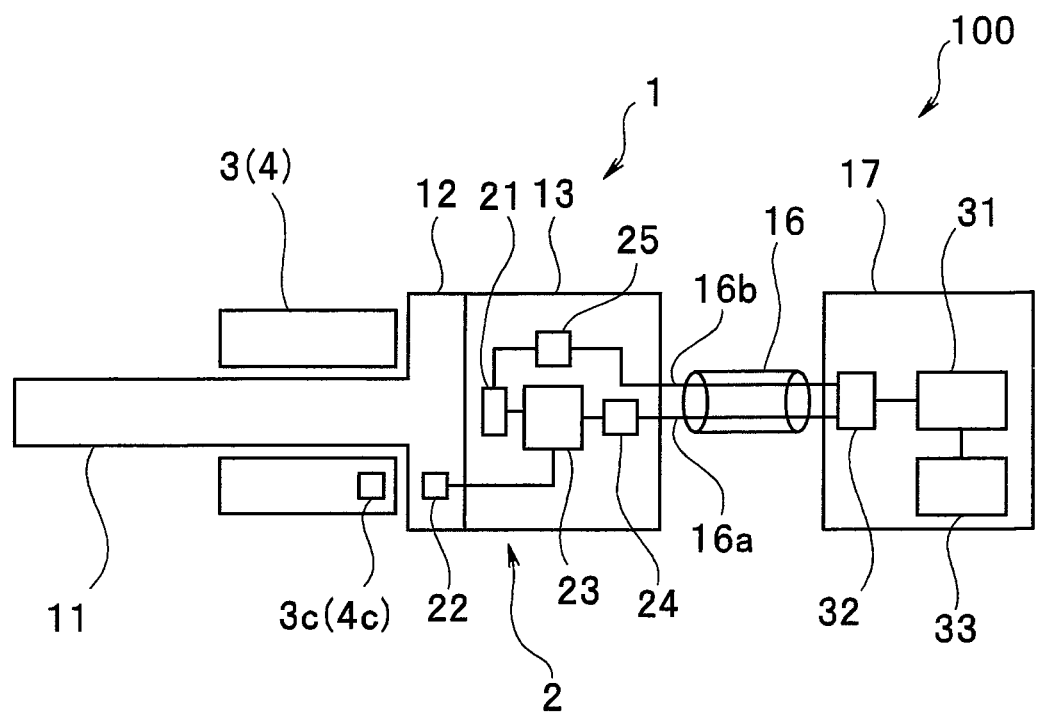
FIG. 4 is a block diagram of a blade inspection system 100 according to the first embodiment.

FIG. 4 is a block diagram of the blade inspection system 100.

The borescope 2 includes the image pickup device 21, a radio signal receiving circuit 22, a control portion 23, and two communication interface circuits 24 and 25. The image pickup device 21 is provided in an image pickup apparatus 13, receives light from an object via various optical systems in the insertion portion 11, photo-electrically converts the light and outputs an image pickup signal to the communication interface circuit 25.

The radio signal receiving circuit 22 is a circuit for receiving a signal of the identification information transmitted wirelessly from the identification information output portions 3c and 4c of the fixtures and for outputting the received signal to the control portion 23. Thus, the radio signal receiving circuit 22 constitutes a detection portion for detecting and receiving the identification information.

The control portion 23 outputs a driving signal for driving the image pickup device and also outputs the identification information received from the radio signal receiving circuit 22 to a signal line 16a of a signal cable 16 via the communication interface circuit 24.

The communication interface circuit 25 outputs an image data signal created by converting the image pickup signal received from the image pickup device 21 to a digital signal to a signal line 16b of the signal cable 16.

That is, the identification information output portions. 3c and 4c are provided in the fixtures 3 and 4 and output the identification information wirelessly, and the borescope 2 has the radio signal receiving circuit 22 which is a radio receiving circuit for wirelessly receiving the identification information outputted from the identification information output portion and outputs the identification information to the PC 17 which is an external apparatus.

Note that explanation of a component other than the above described constituent elements such as an illumination driving circuit will be omitted, here.

The PC 17 includes a control portion 31, a communication interface circuit 32, and a storage device 33.

The control portion 31 includes a central processing unit (CPU), a ROM, a RAM and the like and records image data together with the above described identification information received via the communication interface circuit 32 in the storage device 33 composed of a hard disk apparatus and the like.

The control portion 31 records the inspection image obtained by the blade inspection in a predetermined storage region in the storage device 33 by executing a predetermined processing program stored in the ROM or the storage device 33.

(Operation)

Subsequently, an operation of the blade inspection system 100 of this embodiment will be described.

The fixture transmits a signal of the identification information transmitted wirelessly from the identification information output portion. The borescope 2 transmits the identification information received from the fixture to the PC 17.

As described above, the identification information is for example a port number of the external access port OAP on which the fixture is mounted. Since each of the fixtures is a device dedicated for the corresponding external access port OAP, the identification information output portion of each of the fixtures holds and outputs the identification information such as the port number of the external access port OAP.

Thus, the PC 17 can associate the received inspection image with the external access port OAP to which the image relates on the basis of the received identification information of the fixture and store it in the storage device 33. That is, the PC 17 can store the inspection image associated with the received identification information of the fixture in a folder created in advance in the storage device 33 or store the identification information included in each of the inspection images in the storage device 33.

Note that in the above described example, the identification information of each of the fixtures is supplied to the PC 17 via the borescope 2 but each of the fixtures and the PC 17 may be configured such that the identification information is transmitted to the PC 17 from each of the fixtures via a signal cable different from the signal cable 16. In other words, it may be so configured that each of the fixtures outputs the identification information outputted from the identification information output portion 22 to the PC 17 which is an external apparatus.

Furthermore, the above described blade inspection apparatus 1 is configured such that the insertion portion 11 of the borescope 2 is inserted into the external access port OAP of the engine by using the common borescope 2 and then, the distal end portion of the insertion portion 11 can be positioned at a position for picking up an image of the portion to be observed in the blade in a short time, but each of the fixtures does not have to be configured as such.

Moreover, in the above described example, the common one borescope 2 is inserted into the plurality of fixtures 3, 4 and the like, but separate borescopes may be inserted into each of the fixtures.

Figure 5:
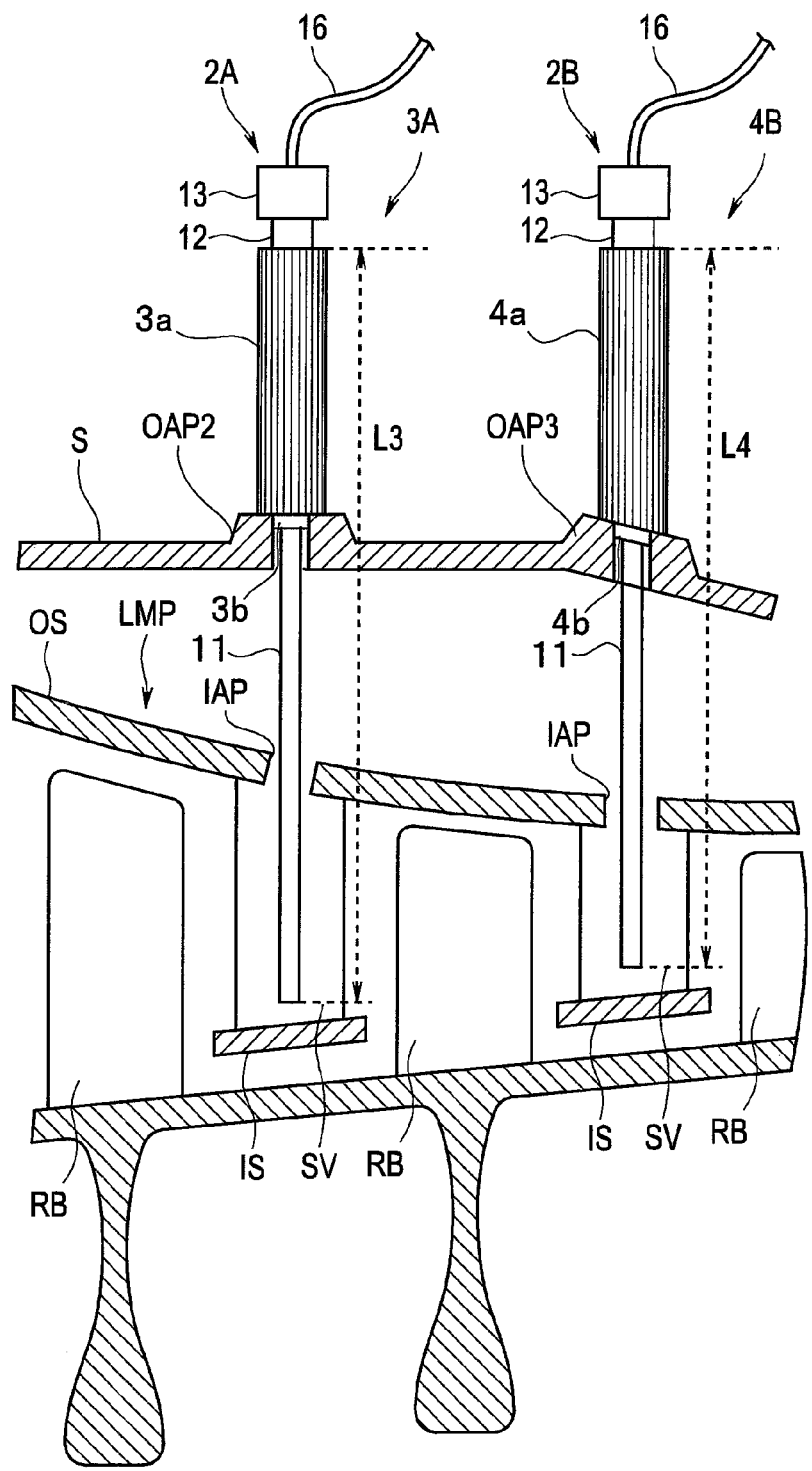
FIG. 5 is a diagram for explaining a state in which a first fixture 3A and a second fixture 4A to which a plurality of borescopes 2A and 2B which are not common, according to the first embodiment, are mounted are attached to the corresponding external access ports, respectively.

FIG. 5 is a diagram for explaining a state in which the first fixture 3A and the second fixture 4A to which the plurality of borescopes 2A and 2B which are not common are attached are mounted on the corresponding external access ports, respectively.

In FIG. 5, lengths of the insertion portions 11 of the borescopes 2A and 2B are different. The length of the insertion portion 11 of the borescope 2A is L3, and the length of the insertion portion 11 of the borescope 2B is L4. Even to a case as FIG. 5, the blade inspection apparatus of this embodiment can be applied.

Moreover, the above described identification information output portion is an IC chip for holding and wirelessly transmitting identification information data, but the identification information output portion may be a circuit or the like that can be read by the borescope 2 via an electrical contact with a resistor having resistance values different for each of the external access ports OAP, combination information of on/off set by a DIP switch or the like.

Subsequently, modifications of detection of the identification information using an output portion capable of detecting with an optical detector, an output portion capable of detecting an electrical resistance value, an output portion capable of outputting a mechanical operation, and an output portion capable of detecting with a magnetic detector as the identification information output portion will be explained.

Figure 6:
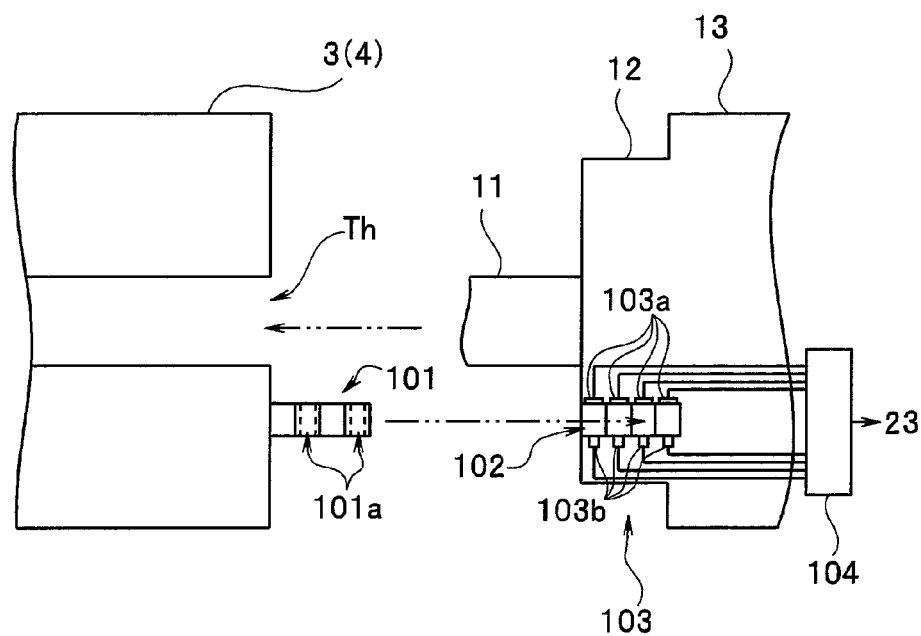
FIG. 6 is a diagram for explaining a configuration of a first modification of a detecting method of identification information in which an identification information output portion for outputting identification information is a member having a portion transmitting light, and an identification information detecting portion uses a sensor for detecting transmission of the light.

A first modification is a detection example of identification information using the optical detector. FIG. 6 is a diagram for explaining a configuration of the first modification of the detecting method of identification information in which the identification information output portion for outputting the identification information is a member having a portion transmitting light, and an identification information detection portion uses a sensor for detecting transmission of the light.

As illustrated in FIG. 6, a rod 101 which is a rod-shaped projection portion is provided on proximal end faces of the fixtures 3 and 4. A hole 102 into which the rod 101 as the identification information output portion can be inserted is formed in the borescope 2.

In the rod 101 which is an identification rod, one or more holes 101a indicating the identification information are formed. In the case of FIG. 6, two holes 101a are formed, and the hole 101a is formed on second and fourth portions from the left. The portion of the hole 101a transmits light, while a portion without the hole 101a does not transmit light. The rod 101 can hold and output 4-bit information as the identification information by setting "1" to the portion transmitting light and "0" to the portion not transmitting light or the like. Since the identification information is 4-bit information, 16 types of the fixtures can be identified.

In the hole 102, a plurality of (four, here) light detecting portions 103 are provided. The light detecting portion 103 as the identification information detecting portion has a plurality of light emitters 103a which are a light emitting device such as a light emitting diode and a plurality of light detectors 103b such as a photo-diode. The plurality of light emitters 103a and the plurality of light detectors 103b are connected to an identification information detection circuit 104. The identification information detection circuit 104 drives the plurality of light emitters 103a, receives inputs of a plurality of light detection signals from the plurality of light detectors 103b, and creates the identification information and outputs it to the control portion 23 on the basis of the inputted plurality of light detection signals.

That is, the rod 101 which is the identification information output portion for outputting the identification information is a member having the portion transmitting light and the portion not transmitting light, and the detecting portion for detecting the identification information is the plurality of light detectors 103b for detecting presence of transmission of light applied to the portion transmitting the light and the portion not transmitting the light.

The rod 101 and the hole 102 are provided on the fixtures 3 and 4 and the borescope 2, respectively, so that the rod 101 is inserted into the hole 102 when the borescope 2 is mounted on the fixture 3.

If there is the hole 101a provided in the rod 101, each of the light detectors 103b detects the light from the corresponding light emitter 103a and outputs a light detection signal, while if there is no hole 101a provided in the rod 101, since the light from the corresponding light emitter 103a is not detected, the light detection signal is not outputted. In the case of the configuration of this modification 1, the identification information of the identification information output portion can be detected in a non-contact manner. Thus, since the one or more holes 101a corresponding to the identification information of the fixtures are formed in the rod 101, the control portion 23 can acquire the identification information of the fixture from the output of the identification information detection circuit 104.

Figure 7:
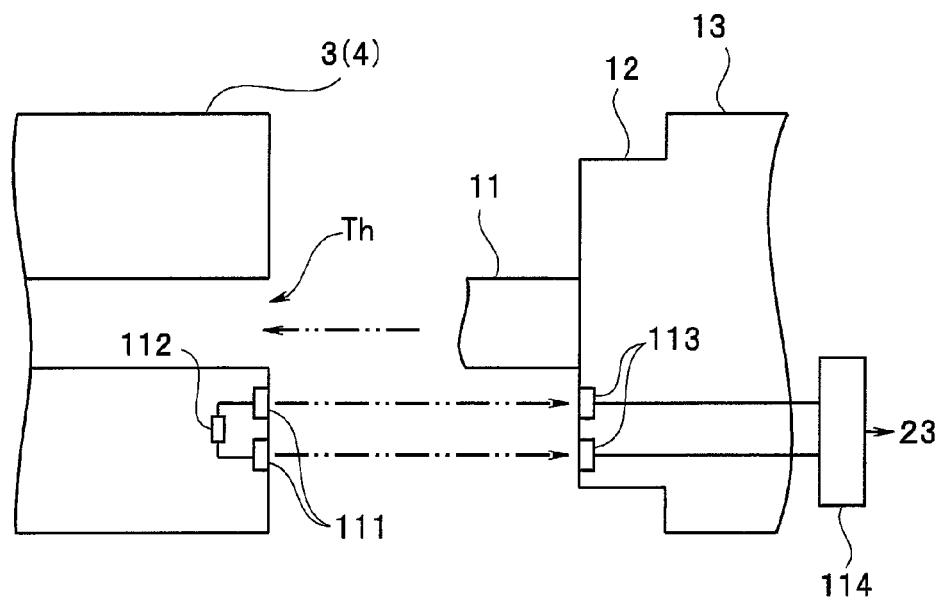
FIG. 7 is a diagram for explaining a configuration of a second modification of a detecting method of identification information in which the identification information output portion for outputting the identification information has a resistor having a resistance value corresponding to the identification information, and the identification information detecting portion uses a sensor for detecting the resistance value.

A second modification is a detection example of identification information using an electrical detector. FIG. 7 is a diagram for explaining a configuration of the second modification of a detecting method of identification information in which the identification information output portion for outputting the identification information has a resistor having a resistance value corresponding to the identification information, and the identification information detection portion uses a sensor for detecting the resistance value.

As illustrated in FIG. 7, two electrical contacts 111 are provided on the proximal end face of the fixture 3 or 4. Inside the fixture 3 or 4, a resistor 112 having a resistance value corresponding to the identification information of its borescope 2 is provided, and both ends of the resistor 112 as the identification information output portion are connected to the two contacts 111.

On the borescope 2, two electrical contacts 113 are formed. The two contacts 113 are connected to an identification information detection circuit 114 as the identification information detecting portion. The identification information detection circuit 114 detects a resistance value between the two contacts 113 and outputs the detected resistance value data to the control portion 23.

That is, the identification information output portion for outputting the identification information includes the resistor 112, and the identification information detection circuit 114 as the detecting portion for detecting the identification information is a resistance value detection circuit for detecting the resistance value of the resistor 112.

When the borescope 2 is mounted on the fixture 3, the two contacts 111 and the two contacts 113 are brought into contact with each other, and the identification information detection circuit 114 outputs the detected resistance value data. Since the identification information is the resistance value, a large number of types of fixtures can be identified. Thus, since the resistor 112 built in each of the borescopes 2 has a resistance value corresponding to the identification information, the control portion 23 can acquire the identification information of the fixture from the output of the identification information detection circuit 114.

Figure 8:
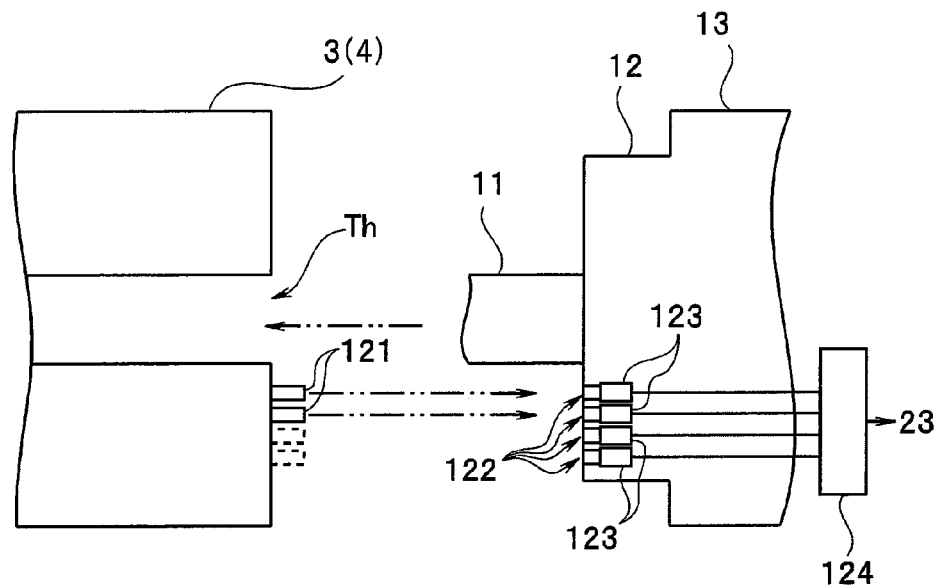
FIG. 8 is a diagram for explaining a configuration of a third modification of a detecting method of identification information in which the identification information output portion for outputting the identification information has one or more pins which are a plurality of projection portions for creating the identification information, and a switch for detecting pressing by each of the pins is used.

A third modification is a detection example of identification information using a mechanical detector. FIG. 8 is a diagram for explaining a configuration of the third modification of a detecting method of identification information in which the identification information output portion for outputting the identification information has one or more pins which are a plurality of projection portions for creating the identification information, and a switch for detecting pressing by each of the pins is used.

As illustrated in FIG. 8, one or more rod-shaped pins 121 are provided on the proximal end faces of the fixtures 3 and 4. In the borescope 2, a plurality of holes 122 into which the pins 121 as the identification information output portion can be inserted is formed, and on a bottom portion of each of the holes 122, a switch 123 as the identification information detecting portion is provided. Outputs of a plurality of (four, here) switches 123 are connected to an identification information detection circuit 124.

The one or more pins 121 indicate the identification information by positions and numbers, and one or more pins 121 corresponding to the identification information are provided on the fixtures 3 and 4.

The switch 123 provided in each of the holes 122 is a micro switch having a highly reliable mechanical mechanism, for example. The identification information detection circuit 124 detects ON/OFF states of the plurality of switches 123, creates the identification information on the basis of the detected states and outputs it to the control portion 23.

The plurality of pins 121 and the plurality of holes 122 are provided on the fixtures 3 and 4 and the borescope 2, respectively, so that, when the borescope 2 is mounted on the fixture 3 or 4, each of the pins 121 is inserted into the corresponding hole 122.

That is, the identification information output portion for outputting the identification information has a projection portion, and the detecting portion for detecting the identification information is a switch for detecting presence of the projection portion.

When each of the pins 121 is inserted into the corresponding hole 122 and presses the switch 123, the information detection circuit 124 detects the ON states corresponding to the positions of the one or more pins 121 provided on the fixtures 3 and 4. If the switch 123 is not pressed by the pin 121, the information detection circuit 124 detects the OFF state. Thus, since the one or more pins 121 corresponding to the identification information of the fixture are formed on the fixtures 3 and 4, the control portion 23 can acquire the identification information of the fixture from the output of the identification information detection circuit 124.

Figure 9:
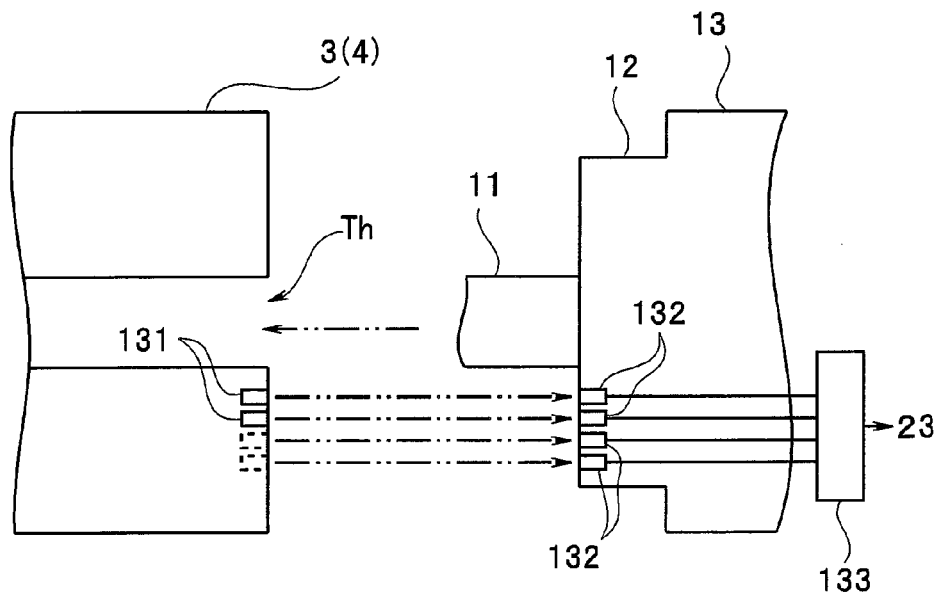
FIG. 9 is a diagram for explaining a configuration of a fourth modification of a detecting method of identification information in which the identification information output portion for outputting the identification information has one or more magnets for creating the identification information and uses a magnetic detector for detecting magnetism by each of the magnets.

A fourth modification is a detection example of identification information using a magnetic detector. FIG. 9 is a diagram for explaining a configuration of the fourth modification of a detecting method of the identification information in which the identification information output portion for outputting the identification information has one or more magnets for creating the identification information, and a magnetic detector for detecting magnetism of each of magnets is used.

As illustrated in FIG. 9, one or more magnets 131 having N-S polarity in an axial direction of the insertion portion 11 are provided on the proximal end faces of the fixtures 3 and 4. In the borescope 2, a plurality of magnetic detectors 132 such as Hall devices corresponding to the one or more magnets 131 provided on the proximal end faces of the fixtures 3 and 4 are provided. Outputs of the plurality of (four, here) magnetic detectors 132 are connected to an identification information detection circuit 133.

The magnet 131 has the polarity of N-S and indicates the identification information by the polarity, and the plurality of (four, here) magnets 131 having the polarities corresponding to the identification information are provided on the fixtures 3 and 4.

The identification information detection circuit 133 detects the outputs of the plurality of magnetic detectors 132, creates the identification information on the basis of the detected output and outputs it to the control portion 23.

The plurality of magnets 131 and the plurality of magnetic detectors 132 are provided on the fixtures 3 and 4 and the borescope 2, respectively, so that each of the magnets 131 gets closer to the corresponding magnetic detector 132 when the borescope 2 is attached to the fixture 3 or 4.

When each of the magnets 131 gets closer to the corresponding magnetic detector 132, the information detection circuit 133 detects the polarity of each of the magnets 131 provided on the fixtures 3 and 4.

Note that creation and detection of the identification information are performed on the basis of the polarity of the magnet, here, but the creation and detection of the identification information may be performed on the basis of presence of the magnet.

That is, the identification information output portion for outputting the identification information includes the magnet 131 and the detecting portion for detecting the identification information is the magnetic detector 132 for detecting the polarity or presence of the magnet.

In the case of the configuration of this modification 4, such merits are provided that the configuration is not only non-contact and difficult to be broken but also is resistant against stains. Thus, since the plurality of magnets 131 having the identification information of the fixture are provided on the fixtures 3 and 4, the control portion 23 can acquire the identification information of the fixture from the output of the identification information detection circuit 133.

As described above, according to this embodiment, the blade inspection apparatus can be provided which can eliminate necessity of an input of information on from which external access port an inspection image is obtained by means of insertion for the inspection image obtained by inserting the endoscope into a plurality of external access ports.

Second Embodiment

In the blade inspection apparatus of the first embodiment, the borescope 2 and each of the fixtures are constituted separately, but in a blade inspection apparatus of a second embodiment, the borescope 2 and each of the fixtures are integrally constituted.

In this embodiment, the same constituent elements as those of the components of the blade inspection system 100 in the first embodiment are given the same reference numerals, and the explanation will be omitted. The blade inspection system of this embodiment has a configuration similar to that of the first embodiment, and a different point is that each of the fixtures is fixed to the borescope 2 and integrated.

Figure 10:
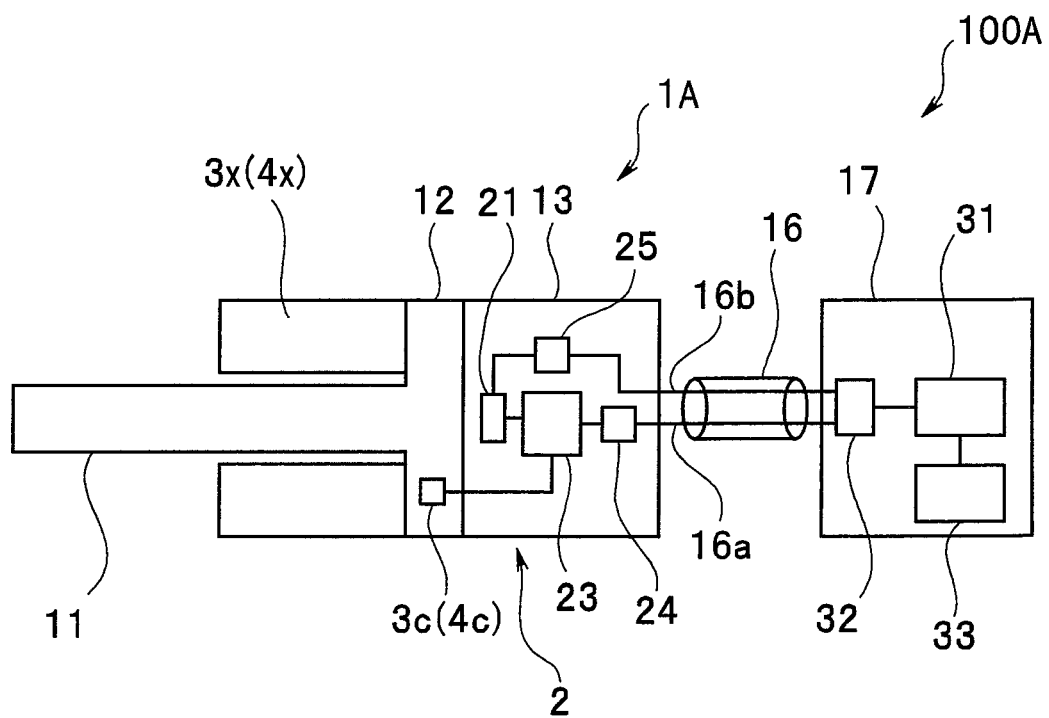
FIG. 10 is a block diagram of a blade inspection system 100A according to a second embodiment of the present invention.

FIG. 10 is a block diagram of a blade inspection system 100A according to this embodiment. In a blade inspection apparatus 1A of this embodiment, a fixture 3x (or 4x) corresponding to the fixture 3 (or 4) explained in the first embodiment is fixed to the borescope 2.

The fixture 3x (or 4x) is fixed to the eyepiece portion 12 of the borescope 2. As illustrated in FIG. 10, the fixture 3x (or 4x) to be attached to the external access port OAP 2 (or OAP 3) is fixed to the eyepiece portion 12. Appearances of the fixtures 3A and 4A to which the borescopes 2 are fixed are the same as the appearance illustrated in FIG. 3 or FIG. 5.

Then, in this case, an identification information output portion 3c (or 4c) is provided on the borescope 2. In the case of FIG. 10, it is provided on the eyepiece portion 12.

An operation of the blade inspection apparatus 1A of this embodiment is the same as the operation of the blade inspection apparatus 1 of the first embodiment. Thus, since the PC 17 can receive the identification information for identifying the external access port OAP, the PC 17 can store an inspection image associated with the received identification information of the fixture in the storage device 33 or store the identification information included in each of the inspection images in the storage device 33.

Note that in the case of this embodiment, the identification information transmitted to the PC 17 may be the identification information of the borescope 2. In that case, by storing information on a correspondence relationship between the borescope 2 and the external access port in the storage device 33 of the PC 17, the control portion 31 can determine from the received identification information of the borescope 2 to which external access port OAP the inspection image relates.

As a result, the control portion 31 can write the number of the external access port or the like in the inspection image or a folder on the basis of the identification information of the endoscope.

As described above, according to this embodiment, a blade inspection apparatus can be provided which can eliminate necessity of an input of information on from which external access port an inspection image is obtained by means of insertion for the inspection image obtained by inserting the endoscope into a plurality of external access ports.

The invention described in the above described embodiment is not limited to the embodiments and modifications, but in addition to that, various modifications can be put into practice within a range not departing from the gist in a practical stage. Moreover, the above described embodiment includes inventions in various stages, and various inventions can be extracted by appropriate combinations in a plurality of disclosed constituent requirements.

What is claimed is:

1. A blade inspection apparatus for inspecting a plurality of blades periodically disposed on a periphery of a rotating shaft of a rotor of an engine and rotated on the rotating shaft, the apparatus comprising:
   an endoscope having an insertion portion in which an observation optical system is provided;
   a plurality of fixtures, each of the plurality of fixtures being dedicated for a respective one of a plurality of external access ports provided on the engine and being configured to be attached to the one of the plurality of the external access ports, for fixing the endoscope; and
   a plurality of identification information output portions, each of the plurality of fixtures being provided with a respective one of the plurality of identification information output portions,
   wherein each of the plurality of identification information output portions holds identification information for identifying the external access port to which its respective fixture is to be attached, and outputs the identification information.

2. The blade inspection apparatus according to claim 1, wherein the endoscope has a detecting portion which detects the identification information outputted from the identification information output portions and outputs the identification information to an external device.

3. The blade inspection apparatus according to claim 2, wherein the identification information output portions output the identification information wirelessly; and
   wherein the detecting portion is a radio receiving circuit for wirelessly receiving the identification information.

4. The blade inspection apparatus according to claim 2, wherein each identification information output portion is a member having a portion transmitting light and a portion not transmitting light; and
   wherein the detecting portion is a light detector for detecting presence of transmission of the light applied to the portion transmitting light and the portion not transmitting light.

5. The blade inspection apparatus according to claim 2, wherein each identification information output portion includes a resistor; and
   wherein the detecting portion is a resistance value detection circuit for detecting a resistance value of the resistor.

6. The blade inspection apparatus according to claim 2, wherein each identification information output portion has a projection portion; and
   wherein the detecting portion is a switch for detecting presence of the projection portion.

7. The blade inspection apparatus according to claim 2, wherein each identification information output portion includes a magnet; and
   wherein the detecting portion is a magnetic detector for detecting a polarity or a presence of the magnet.

8. The blade inspection apparatus according to claim 1, wherein each fixture outputs the identification information outputted from its respective identification information output portion to an external device.

9. The blade inspection apparatus according to claim 1, wherein a plurality of the endoscopes are provided, each endoscope being integrally constituted with a respective one of the plurality of fixtures.

10. The blade inspection apparatus according to claim 1, wherein the identification information is a port number of the external access port to which the fixture from among the plurality of fixtures is to be attached.

11. The blade inspection apparatus according to claim 1, further comprising an external device for receiving the identification information,
    wherein the external device stores an inspection image in a storage device while associating the inspection image with the external access port based on the received identification information.

12. The blade inspection apparatus according to claim 11, wherein the external device stores the inspection image in a folder created in the storage device based on the received identification information.

13. The blade inspection apparatus according to claim 11, wherein the external device stores the inspection image in the storage device, with the inspection image including the received identification information.

14. The blade inspection apparatus according to claim 1, wherein each the plurality of fixtures has a shape corresponding to the respective one of the plurality of external access ports for which it is dedicated, the shapes being different from each other; and
    wherein each of the plurality of fixtures has a length along an axial direction of a body portion thereof based on the respective one of the plurality of external access port for which it is dedicated, the lengths being different from each other.

15. The blade inspection apparatus according to claim 1, wherein each identification information output portion outputs its identification information when the insertion portion is attached to the endoscope.

* * * * *